US00PP17077P3

(12) United States Plant Patent
Trees

(10) Patent No.: US PP17,077 P3
(45) Date of Patent: Sep. 5, 2006

(54) ***LOBELIA* PLANT NAMED 'BALOBPERIBLU'**

(50) Latin Name: *Lobelia hybrida*
Varietal Denomination: Balobperiblu

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/017,175

(22) Filed: Dec. 20, 2004

(65) Prior Publication Data

US 2006/0137059 P1 Jun. 22, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Louanne Krawczewicz Myers
(74) *Attorney, Agent, or Firm*—Wood, Phillips, Katz, Clark & Mortimer

(57) ABSTRACT

A new and distinct cultivar of *Lobelia* plant named 'Balobperiblu' characterized by its mounded and trailing growth habit, dark lavender blue-colored flowers with white "eye", dark green-colored foliage, and day length neutral flowering habit.

1 Drawing Sheet

Latin name of genus and species of plant claimed: *Lobelia hybrida.*
Variety denomination: 'Balobperiblu'.

BACKGROUND OF THE INVENTION

The present invention relates to a new and distinct *Lobelia* plant hereinafter referred to by the cultivar name 'Balobperiblu'.

This new cultivar originated in a controlled breeding program during August 2001 at Arroyo Grande, Calif. The objective of the breeding program was the development of new *Lobelia* cultivars with unique flower colors, and vigorous and trailing growth habits.

The new cultivar was the result of the self-pollination of the *Lobelia hybrida* cultivar Periwinkle Blue, U.S. Plant Pat. No. 12,536, which exhibits large, sky blue-colored flowers with white 'eye', a vigorous growth habit, and is extremely floriferous. The resulting seed was collected and germinated. From the flowering progeny, a single plant was discovered and selected by the inventor during January 2002.

Asexual reproduction of the new cultivar by terminal stem cuttings since January 2002 at Arroyo Grande, Calif., and West Chicago, Ill., has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

The following characteristics of the new cultivar have been repeatedly observed and can be used to distinguish 'Balobperiblu' as a new and distinct cultivar of *Lobelia* plant:

1. Mounded and trailing growth habit.
2. Dark lavender blue-colored flowers with white "eye".
3. Dark green-colored foliage.
4. Day length neutral flowering habit.

Of the *Lobelia* cultivars known to the inventor, the most similar to the new cultivar is the *Lobelia* cultivar Periwinkle Blue, U.S. Plant Pat. No. 12,536. However in side-by-side comparisons, plants of the new cultivar differ from plants of 'Periwinkle Blue' in the following characteristics:

1. Plants of the new cultivar have a more spreading growth habit than plants of 'Periwinkle Blue'.
2. Plants of the new cultivar have shorter internodes than plants of 'Periwinkle Blue'.
3. Plants of the new cultivar have smaller flowers than plants of 'Periwinkle Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balobperiblu'. The plants were grown in 10 cm pots for 14 weeks in a greenhouse at West Chicago, Ill.

DETAILED BOTANICAL DESCRIPTION

Figure 1:
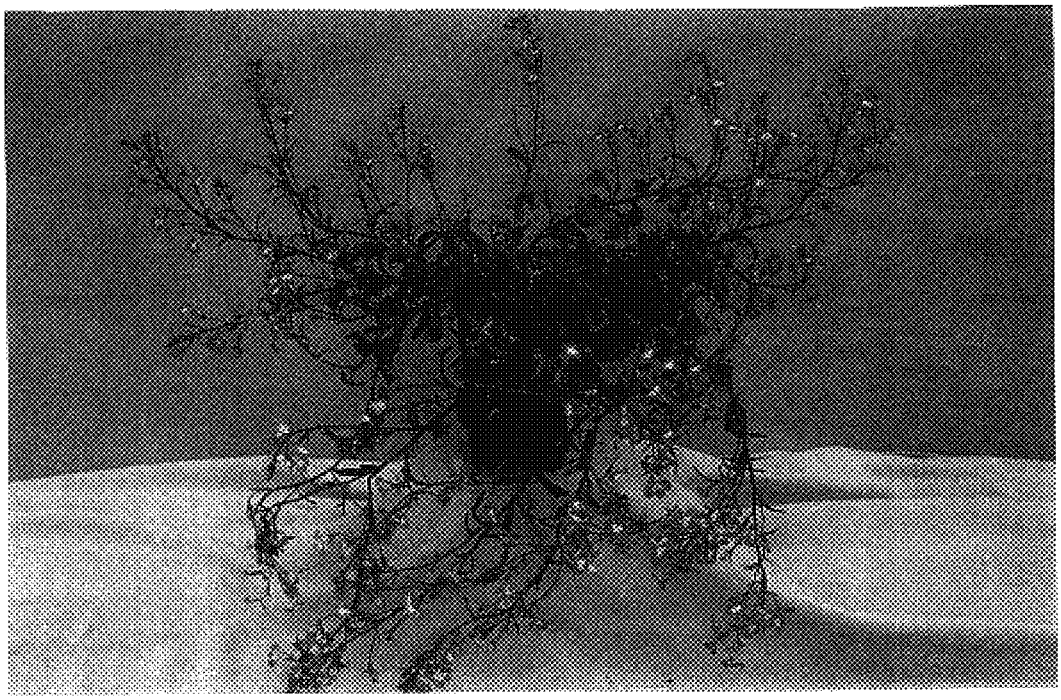
FIG. 1 illustrates a side view of the general growth and flowering habit of 'Balobperiblu'.
Figure 2:
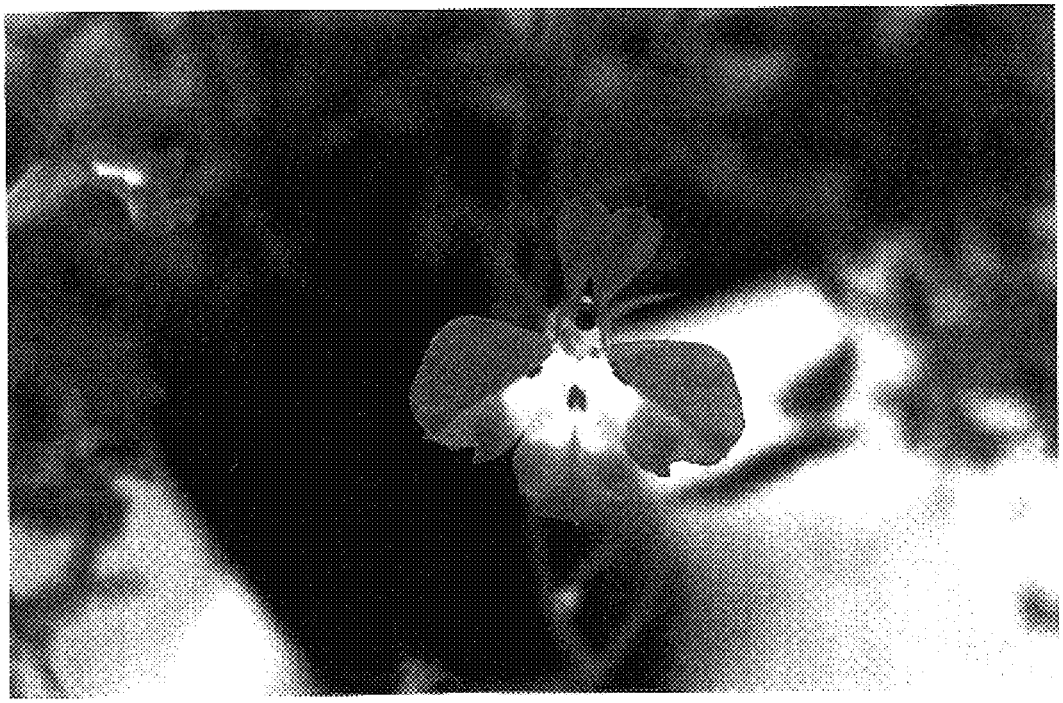
FIG. 2 illustrates a close-up view of a single flower of 'Balobperiblu'.

The chart used in the identification of colors described herein is The R.H.S. Colour Chart of The Royal Horticultural Society, London, England, 2001 edition, except where color terms of ordinary significance are used. The color values were determined on Sep. 27, 2004 in West Chicago, Ill. between 1:00 and 1:45 p.m. under natural light conditions.

The following descriptions and measurements describe plants produced from cuttings taken from stock plants and grown in a double polycarbonate-covered under greenhouse under conditions comparable to those used in commercial practice. Plants were grown in 10 cm pots for 14 weeks while utilizing a soil-less growth medium. Greenhouse temperatures were maintained at approximately 70–80° F. (21–26° C.) during the day and approximately 55–65° F. (13–18° C.) during the night. Greenhouse light levels were maintained at approximately 5,000–8,000 footcandles during the day.

Botanical classification: *Lobelia hybrida* cultivar 'Balobperiblu'.

Parentage:

*Parent.*—'Periwinkle Blue', U.S. Plant Pat. No. 12,536.

Propagation:

*Type cutting.*—Terminal stem.

*Time to initiate roots.*—Approximately 6–9 days.

*Time to produce a rooted cutting.*—Approximately 28 days.

*Root description.*—Fibrous.

*Rooting habit.*—Freely branching.

Plant description:

*Crop time.*—Approximately 8–10 weeks.

*Growth habit.*—Vigorous and freely branching with lateral branches at every node.

*Form.*—Mounded trailing.

*Size.*—Height from soil level to top of plant plane: Approximately 19.5 cm. Diameter (area of spread): Approximately 55.5 cm.

Branch description: Quantity of main branches: 5. Strength: Strong, pliable. Shape: Square in cross section. Length: Approximately 35.1 cm. Diameter: Approximately 2.1 mm. Texture: Sparse pubescence along edges. Color: Closest to 144A. Length of center internode: Approximately 1.7 cm.

Foliage: Quantity of leaves per main branch: Approximately 16. Fragrance: None. Form: Simple. Arrangement: Alternate. Aspect: At acute angle to the stem. Base: Decurrent. Texture: Glabrous except for spare pubescence along veins and margin.

Upper leaves: Shape: Linear. Apex: Mucronate. Margin: Entire. Length: Approximately 3.2 cm. Width: Approximately 6.3 mm. Venation pattern: Pinnate. Color of upper surface of mature foliage: Closest to 137B with venation of 145B. Color of lower surface of mature foliage: Closest to 137D overlaid with venation of 145B.

Lower leaves: Shape: Spatulate. Apex: Mucronate. Margin: Lobed. Length: Approximately 3.3 cm. Width: Approximately 1.9 mm. Color of upper surface of mature foliage: Closest to 137B with venation of 154B. Color of lower surface of mature foliage: 137D with venation of 145B.

Flowering description:

*Flowering habit.*—'Balobperiblu' is freely flowering under outdoor growing conditions with substantially continuous blooming from spring until autumn and year round in greenhouse environment.

*Lastingness of bloom.*—5–7 days.

*Inflorescence type.*—Single, simple.

*Quantity of flowers per flowering branch.*—Approximately 62.

Flower description:

*Flower bud.*—Rate of opening: Generally takes 3–6 days for buds to progress from first color to fully open flower. Shape: Oblong. Length: Approximately 1.1 cm. Diameter at apex: Approximately 3.6 mm. Diameter at base: Approximately 2 mm. Texture: Glabrous. Color of tube: 155B. Color of petals: Slightly lighter than 122B.

*Flower aspect.*—Pointing outwardly, inverted because of twisted pedicel.

*Flower form.*—Ampliate, labiate, upper lip consists of two narrow petals; lower lip consists of three broader petals. Petals are fused at base forming a tube which is split between the two upper petals.

*Flower size.*—Diameter/width: Approximately 1.2 cm. Length: Approximately 1.3 cm. Depth: Approximately 1.1 cm.

*Corolla tube.*—Split almost to base along one side. Length: Approximately 1 cm. Diameter at base: Approximately 2 mm. Diameter at throat: Approximately 3.5 mm. Texture of outer surface: Glabrous. Texture of inner surface: Pubescent. Color of outer and inner surface: Closest to N155A with spots of N88B.

*Petals.*—Margin: Entire.

*Upper petals.*—Shape: Narrow obovate. Apex: Mucronate. Length: 5 mm. Width at apex: 1.8 mm. Texture of upper and lower surfaces: Glabrous. Color of upper surface: Closest to but slightly redder than 96D in center, gradually transitioning to 94D at margin. Color of lower surface: Closest to 92C.

*Lower petals.*—Shape: Broadly obovate. Apex: Mucronate. Length: 7 mm. Width at apex: 4 mm. Texture of upper and lower surfaces: Glabrous with cilia along margin. Color of upper surface: Outer ½ of all petals is closest to but redder than 96A. Central petal, from throat ⅔ of the way to margin, and inner edge of lateral lower petals is N155A. Central petal at margin: 94D with two spots of 94A in center. Color of apex and outer margin of lateral lower petals: Closest to but slightly redder than 96D with 94D at margin and spot of 94A in center of each lateral lower petal. Color of lower surface of central petal: 92C at apex, N155A at base. Color of lower surface of lateral lower petals: 92C at apex and outer margin, 155A at base and along inner margin.

*Peduncle.*—Strength: Strong. Length: Approximately 6 cm. Diameter: Approximately 2 mm. Texture: Glabrous. Color: 144A.

*Pedicel.*—Strength: Strong. Length: Approximately 1.8 cm. Diameter: Approximately 0.6 mm. Texture: Glabrous. Color: Closest to 137B.

*Calyx.*—Formed by 5 sepals fused at base. Shape: Star. Length: Approximately 9.4 mm. Diameter at base: Approximately 1.6 mm. Diameter at petals: Approximately 9.3 mm. Sepal shape: Linear. Sepal apex: Acute. Sepal margin: Entire. Texture of upper and lower surface of sepal: Glabrous. Color of upper and lower surface of sepal: 137C.

*Reproductive organs.*—Stamen quantity: 5. Filament color: N155A. Anthers fused around pistil. Anther length: Approximately 1.6 mm. Anther color: N92A. Pollen amount: Moderate. Pollen color: 155B. Pistil quantity: One. Length: Approximately 1.2 cm. Stigma shape: Bi-lobed. Stigma length: 1 mm.

Stigma color: 83B. Style length: 7 mm. Style color: 144C. Ovary size: 4 mm. Ovary color: 144C.

Seed and fruit development: Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balobperiblu', substantially as herein illustrated and described.

* * * * *